US00PP20503P2

(12) United States Plant Patent
Jandrew

(10) Patent No.: US PP20,503 P2
(45) Date of Patent: Nov. 24, 2009

(54) ***PENSTEMON* PLANT NAMED 'PENI ABLOS09'**

(50) Latin Name: *Penstemon hartwegii benth*
Varietal Denomination: Peni Ablos09

(75) Inventor: Jason Jandrew, Gilroy, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 12/229,106

(22) Filed: Aug. 20, 2008

(51) Int. Cl.
*A01H 5/00* (2006.01)

(52) U.S. Cl. ..... Plt./465

(58) Field of Classification Search ..... Plt./465
See application file for complete search history.

*Primary Examiner*—Annette H Para
(74) *Attorney, Agent, or Firm*—S. Matthew Edwards

(57) ABSTRACT

A new *Penstemon* plant named 'Peni Ablos09,' particularly distinguished by large, white flower color with a red-pink margin, upright and semi-compact plants, strong stems, and earlier flowering habit.

1 Drawing Sheet

Latin name of the genus and species of the plant claimed: *Penstemon hartwegii benth.*

Varietal denomination: 'Peni Ablos09'.

BACKGROUND OF THE NEW PLANT

The present invention comprises a new *Penstemon,* botanically known as *Penstemon hartwegii,* and hereinafter referred to by the variety name 'Peni Ablos09.'

'Peni Ablos09' is a product of a planned breeding program. The new cultivar 'Peni Ablos09' has large, white flower color with a red-pink margin, upright and semi-compact plants, strong stems, and earlier flowering habit.

'Peni Ablos09' originated from an hybridization in a controlled breeding program in Gilroy, Calif. USA. The female parent was an unpatented hybrid seedling identified as '11-1' with dusty rose color. '11-1' has a less compact habit and is later to flower than 'Peni Ablos09.'The male parent of 'Peni Ablos09' was an unpatented hybrid seedling identified as '104-1' with apple blossom color. '104-1' has a lighter foliage color, a less compact habit, and is later to flower than 'Peni Ablos09.'

'Peni Ablos09' was selected as one flowering plant within the progeny of the stated cross in 2006 in a controlled environment in Gilroy, Calif. USA.

The first act of asexual reproduction of 'Peni Ablos09' was accomplished when vegetative cuttings were taken from the initial selection in the April 2006. The pollination was made in July 2005 and the seed sowing took place in October 2005 in a controlled environment in Gilroy, Calif. USA.

Horticultural examination of plants grown from cuttings of the plant initiated in April 2006 in Gilroy, Calif. USA, and continuing thereafter, has demonstrated that the combination of characteristics as herein disclosed for 'Peni Ablos09' are firmly fixed and are retained through successive generations of asexual reproduction.

'Peni Ablos09' has not been observed under all possible environmental conditions. The phenotype may vary significantly with variations in environment such as temperature, light intensity and day length.

A Plant Breeder's Right for this cultivar was applied for in Canada on Dec. 24, 2007. 'Peni Ablos09' has not been made publicly available more than one year prior to the filing of this application.

DESCRIPTION OF THE DRAWING

The accompanying photographic drawing shows typical flower and foliage characteristics of 'Peni Ablos09' with colors being as true as possible with an illustration of this type. The photographic drawing shows a flowering potted plant of the new variety and a close-up of the flowers.

DETAILED BOTANICAL DESCRIPTION

The measurements were taken in the spring of April 2008, on plants that were growing in 1 gallon pots in a greenhouse in Gilroy, Calif. USA. Culture of these plants started in about January 2008 in a greenhouse. The plants were about 4 months old.

Color Chart used: Royal Horticultural Society Colour Chart (R.H.S.) 2001

BRIEF SUMMARY OF INVENTION

The following observations, measurements, and comparisons describe plants grown a greenhouse in Gilroy, Calif. USA. The following traits have been repeatedly observed and are determined to be basic characteristics of the new variety. The combination of these characteristics distinguishes this *Penstemon* as a new and distinct variety.

TABLE 1

DIFFERENCES BETWEEN THE NEW VARIETY 'PENI ABLOS09' AND A SIMILAR VARIETY

| | 'Peni Albos09' | 'Pheni Ablos' (U.S. Plant Pat. No. 17,971) |
|---|---|---|
| Branching | More branching | Fewer branching |
| Flowering response | Earlier | Later |
| Habit | More compact | Less compact |

Plant:

*Form, growth and habit.*—Upright, semi-compact, strong branching and vigor

*Plant height.*—28–32 cm.

*Plant height (inflorescence included).*—48–52 cm.

*Plant width.*—38–42 cm.

Foliage:

*Arrangement.*—Opposite and decussant.

*Immature, leaf color, upper surface.*—Closest to RHS 137D. Lower surface: Closest to RHS 147B.

*Mature, leaf color, upper surface.*—RHS 137B. Lower surface: Closest to RHS 147B.

*Length.*—13.6–14.8 cm.

*Width.*—2.7–3.4 cm.

*Shape.*—Lanceolate.

*Base.*—Sessile.

*Apex shape.*—Acute.

*Margin.*—Very slightly serrate.

*Texture.*—Slightly pubescent on both sides.

*Color of veins, upper surface.*—RHS 144C.

*Color of veins, lower surface.*—RHS 144C.

Stem:

*Number of main stems per plant.*—About 5.

*Number of leaves per branch.*—About 18–20.

*Color of stem.*—RHS 144A.

*Length of stem.*—25–30 cm.

*Diameter.*—0.4–0.5 cm.

*Length of internodes.*—1.5–3.0 cm.

*Texture.*—Pubescent.

Inflorescence:

*Type.*—On first flowering it appears to be a raceme, then matures to more of a thyrse with short peduncles emerging at the nodes in opposite arrangement, each peduncle bearing 5–7 flowers or buds at various stages of development; the flowers are held somewhat horizontally.

*Blooming habit.*—Intermittent; removing of spent flowers enhances development of new flowers.

*Number of inflorescences per plant.*—6–8; early terminal pinching of apices enhances formation of more racemes.

*Raceme color.*—RHS 144B.

*Raceme length.*—16–25 cm.

*Raceme texture.*—Pubescent.

*Color of peduncle.*—RHS 144B.

*Length of peduncle.*—0.5–0.6 cm.

*Diameter peduncle.*—0.15 cm

*Texture.*—Pubescent to hirsute.

*Color of pedicel.*—RHS 144B.

*Length of pedicel.*—0.4–0.6 cm.

*Diameter of pedicel.*—0.1 cm.

*Texture.*—Pubescent to hirsute.

Corolla:

*Form.*—Zygomorphic and single; funnel-shaped with the petals fused at base, 5 free lobed, opening outward.

*Fragrance.*—None.

*Lastingness of individual florets.*—About 7 days.

*Width of floret.*—3.3–3.7 cm.

*Depth of floret.*—3.3–3.5 cm.

*Color upper lobes, upper surface.*—RHS N155B but a little whiter; with a slight hint of RHS 52D but lighter at the margins.

*Color upper lobes, lower surface.*—RHS N155B but whiter.

*Length of upper lobes.*—1.0–1.1 cm.

*Width of upper lobes.*—1.3–1.5 cm.

*Color lateral lobes, upper surface.*—Same as upper.

*Color lateral lobes, lower surface.*—Same as upper.

*Length of lateral lobes.*—1.1–1.2 cm.

*Width of lateral lobes.*—1.4–1.7 cm.

*Color lower mid-lobe, upper surface.*—Same as upper.

*Color lower mid-lobe, lower surface.*—Same as upper.

*Length of lower mid-lobe.*—1.2–1.3 cm.

*Width of lower mid-lobe.*—1.5–1.7 cm.

*Apex shape.*—Rounded.

*Margin.*—Entire.

*Petal texture.*—Pubescent; glandular hairs on both surfaces.

*Corolla color, inside.*—RHS N155B but whiter.

*Corolla color, outside.*—RHS N155B but whiter; sometimes blushed RHS 52C on the top of the corolla; RHS 71 C basally at the calyx.

*Corolla length.*—3.0–3.3 cm.

Bud (just before opening):

*Color.*—RHS 144D some a little lighter; RHS 52A to B at apex.

*Length.*—1.7–2.2 cm.

*Width.*—1.0–1.2 cm.

*Shape.*—Oblong.

*Number of sepals.*—5, fused at base.

*Color of sepals.*—RHS 144B.

*Length of sepals.*—0.7–0.8 cm.

*Width of sepals.*—0.3–0.6 cm.

*Sepal shape.*—Ovate.

*Apex shape.*—Acute.

*Margins.*—Entire.

*Texture.*—Pubescent; glandular hair (on both surfaces).

Reproductive organs:

*Pistil.*—1.

*Style color.*—RHS N155B but whiter.

*Style length.*—3.1–3.2 cm.

*Stigma color.*—RHS 54C.

*Number of anthers.*—5, 4 of which are fertile.

*Color of filaments.*—RHS N155b but whiter.

*Length of filaments.*—3.0–3.2 cm.

*Pollen amount.*—Abundant.

*Color of pollen.*—RHS 158A.

*Fertility/seed set.*—Not observed on this hybrid.

Disease/pest resistance: Disease resistance and/or susceptibility has not been observed on this hybrid.

What is claimed is:

1. A new and distinct variety of *Penstemon* plant named 'Peni Ablos09,' substantially as illustrated and described herein.

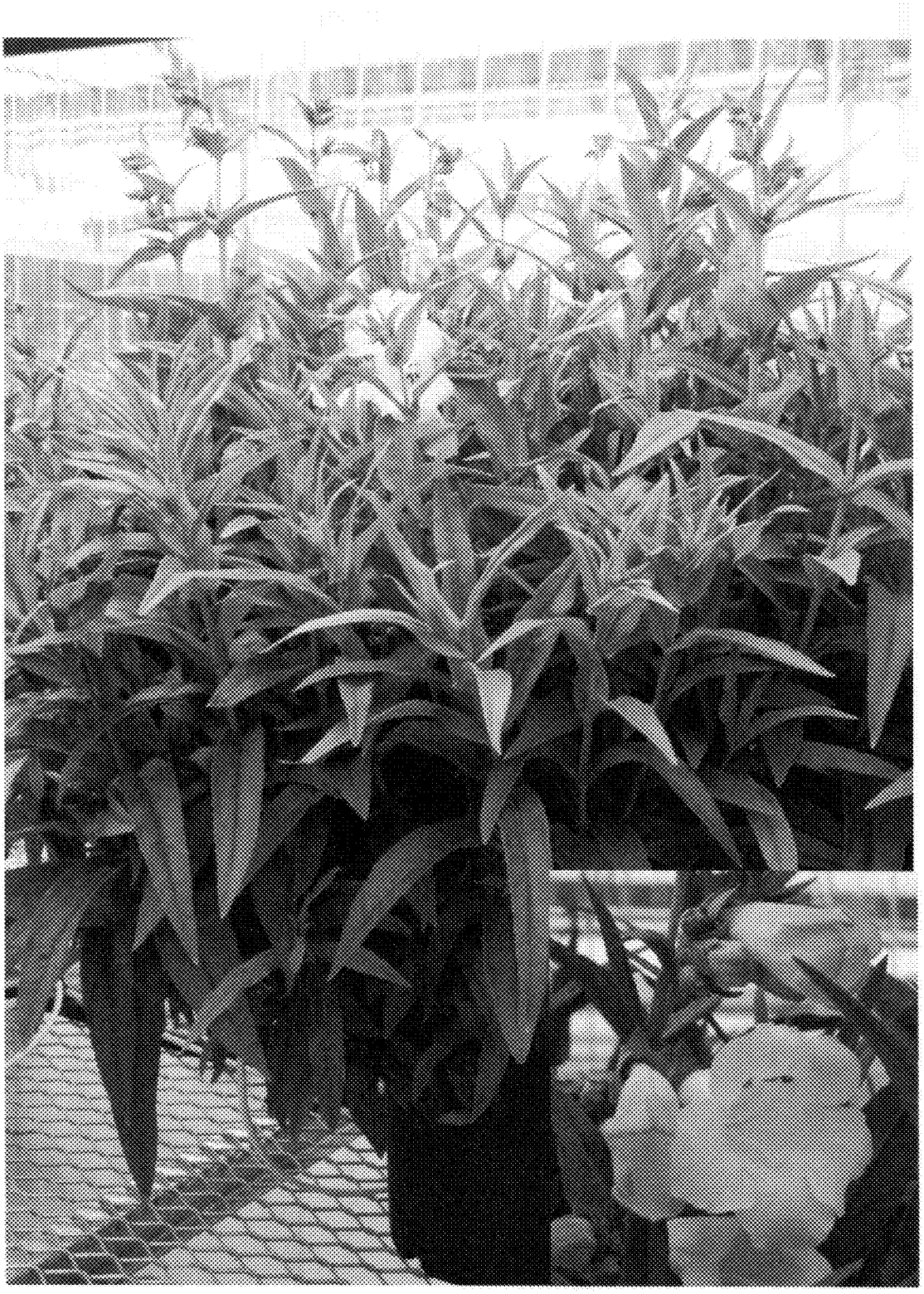

* * * * *